(12) United States Patent
Bollinger et al.

(10) Patent No.: US 6,433,293 B1
(45) Date of Patent: Aug. 13, 2002

(54) METHOD AND DEVICE FOR DETECTING DIRT AS PRESENT ON ARTICLES, FOR EXAMPLE EGGS

(75) Inventors: Peter Bollinger, Boppard; Wolfgang Pomrehn, Wiehl, both of (DE)

(73) Assignee: FPS Food Processing Systems B.V. (NL)

( * ) Notice: Subject to any disclaimer, the term of this patent is extended or adjusted under 35 U.S.C. 154(b) by 0 days.

(21) Appl. No.: 09/554,655

(22) PCT Filed: Nov. 19, 1998

(86) PCT No.: PCT/NL98/00666

§ 371 (c)(1),
(2), (4) Date: Jul. 19, 2000

(87) PCT Pub. No.: WO99/27362

PCT Pub. Date: Jun. 3, 2000

(30) Foreign Application Priority Data

Nov. 20, 1997 (EP) .............................................. 97203600

(51) Int. Cl.[7] .......................... G01N 21/64; A01K 43/00
(52) U.S. Cl. ....................... 209/511; 209/578; 209/936; 250/461.1
(58) Field of Search ................................. 209/511, 510, 209/578, 939, 936, 938; D10/48; 250/461.1

(56) References Cited

U.S. PATENT DOCUMENTS

| | | | | |
|---|---|---|---|---|
| 4,039,259 A | * | 8/1977 | Saito et al. ................... 356/53 |
| 4,161,366 A | * | 7/1979 | Bol et al. ....................... 356/56 |
| 4,390,787 A | * | 6/1983 | Jennings et al. .......... 250/459.1 |
| 4,591,723 A | * | 5/1986 | Akiyama ................. 250/461.1 |
| 4,622,469 A | * | 11/1986 | Aklyama ..................... 250/458 |
| 4,713,781 A | * | 12/1987 | Brizgis et al. .............. 382/110 |
| 4,805,778 A | * | 2/1989 | Nambu ........................ 209/3.3 |
| 4,866,283 A | * | 9/1989 | Hill, Jr. |
| 4,872,564 A | * | 10/1989 | van der Schoot ........... 209/511 |
| 4,884,696 A | * | 12/1989 | Peleg .......................... 209/545 |
| 5,030,001 A | * | 7/1991 | vande Vis ..................... 356/53 |
| 5,237,407 A | * | 8/1993 | Crezee et al. ................. 348/89 |
| 5,277,320 A | * | 1/1994 | Corkill et al. .............. 209/511 |

FOREIGN PATENT DOCUMENTS

| | | | | |
|---|---|---|---|---|
| DE | 236665 | * | 6/1985 | .................. 209/510 |
| EP | 398444 A1 | * | 11/1990 | .......... G01N/33/08 |
| EP | 554954 A1 | * | 8/1993 | ........... B07C/5/342 |
| GB | 2187277 A | * | 9/1987 | .................. 209/511 |
| JP | 09129987 | * | 5/1994 | .......... G01N/21/64 |

* cited by examiner

Primary Examiner—Donald P. Walsh
Assistant Examiner—Daniel K Schlak
(74) Attorney, Agent, or Firm—Larson & Taylor, PLC

(57) ABSTRACT

Method and device for detecting dirt on eggs is provided which comprises exposing the eggs to ultraviolet light, capturing images of the exposed eggs resulting in images formed of pixels, and determining within the images, surface areas of dirt by correlating data of contrast and data of position of the pixels. Such a method enables selecting and subsequently removing eggs which contain dirt surface areas of a predetermined size. Further, such a method and device may be applied advantageously for both white and brown eggs in egg sorting machines.

26 Claims, 1 Drawing Sheet

METHOD AND DEVICE FOR DETECTING DIRT AS PRESENT ON ARTICLES, FOR EXAMPLE EGGS

FIELD OF THE INVENTION

The present invention relates to a method and device for detecting dirt on eggs, comprising exposing said eggs to ultraviolet light. In particular the invention concerns a method and a device for selecting and sorting eggs upon which dirt is detected

DESCRIPTION OF THE RELATED ART

In the field of industrial activity of egg processing it is well known to examine eggs and subsequently to select eggs on certain characteristics for which well-defined criteria are set. The characteristics are mainly weight and crack condition.

In present times of very large and still growing egg processing plants standards on hygienic in treatment of food products are becoming more stringent, for example in regard to dirt on eggs. Remnants of dirt, in particular remnants of albumen and yolk, and also traces of excrements, can cause unwanted infections and consequently can be very disadvantageous during and after processing of eggs. Before removing dirt on eggs, or even to remove dirty eggs as well, it is necessary to detect the dirt adequately and to incorporate this detection in egg sorting procedures.

Historically, see for example the German patent DE 937956, eggs are inspected, more in particular "candled", before the eggs are sorted. During conveying by a sorting machine, the eggs are exposed to white light from below, mainly in order to make blood spots or cracks visible. Then eggs can be either labeled or removed by hand. In case of sorting such labels are taken into account.

From U.S. Pat. No. 4,622,469 it is known to detect remnants of rotten albumen by exposing eggs to ultraviolet light. The rotten albumen may, for example, originate from broken eggs. According to this patent, such remnants are fluorescent.

In OSRAM-catalogue, named "Lichtprogramm 97/98", page 6.12, high-pressure mercury lamps are disclosed as ultraviolet light sources to be used for recognizing remnants of dirt on fruit, meat, fish, etc. From this reference, it is not clear to what extent contrasts in fluorescent image areas can be distinguished.

From Patent Abstracts of Japan Publication Number 56-145350, a stained part of the eggshell is made to fluorescence thereby providing for dirt detection. A disadvantage of the 56-145350 method is that the sorting and selecting of the eggs is rather inaccurate.

SUMMARY OF THE INVENTION

The main object of the present invention is to take measures in order to satisfy the above-mentioned standards and criteria, thereby also remedying the shortcomings of the methods and devices known thus far.

Therefore the present invention involves a method as mentioned above, further comprising, capturing images of exposed eggs, the images comprising pixels, and determining within the images surface areas of dirt on the basis that egg shells are clearly fluorescent whereas a dirt surface is not fluorescent by correlating data of contrast and data of position of said pixels.

In the present method, the dirt areas appear dark or black. Determination of dirt areas is therefore made on the basis that the dirt surface is clearly fluorescent and the dirt surfaces are not fluorescent, rather than on the basis that the dirt fluoresces.

It has appeared that for both brown and white eggs, when exposed to ultraviolet light, the egg shells are clearly fluorescent whereas the dirt surface areas are not fluorescent. The resulting differences in fluorescence at different parts of the egg surface allow one to obtain contrast data for article surface areas. Consequently by having such data, such surface parts can be compared with present standards and suitable decisions about further treatment and processing can be taken.

Advantageously the invention can be applied for automatic sorting and selecting procedures for large amounts of articles such as eggs. Differences in such sorting and selecting caused by interpretation or tiredness of operators who sort such articles by hand, can be avoided. Moreover, different settings according to correspondingly different requirements, for example as to brightness, can easily be employed.

Another advantage of the present invention is found in inspection of articles already cleaned. Thus dirt which hardly could be observed using conventional methods can be traced.

In another embodiment of the present invention said articles are positioned upon rollers of a conveyor or a conveyor belt in that said articles are rotating about an axis. Either continuous, intermittent, or pulsing exposure, or even combinations, can be employed advantageously in the set-up of the present invention.

Patent Abstract of Japan, publication number 06129987 discloses a method to excite a damaged part of an oil cell for emission by inactivating the surface of citrus fruits etc. with an ultra violet ray. The light is captured with a camera for picture processing. The reference does not disclose a method on the basis of eggshells clearly being fluorescent rather than a dirt surface area looking black.

EP 0 398 444 discloses a method for detecting dirt etc. on egg shells by scanning the egg with a beam light and subsequent detection of the egg by means of a camera.

BRIEF DESCRIPTION OF THE SEVERAL VIEWS OF THE DRAWINGS

Hereinafter the invention will be explained in detail, thereby referring to.

DETAILED DESCRIPTION OF THE INVENTION

Figure 1:
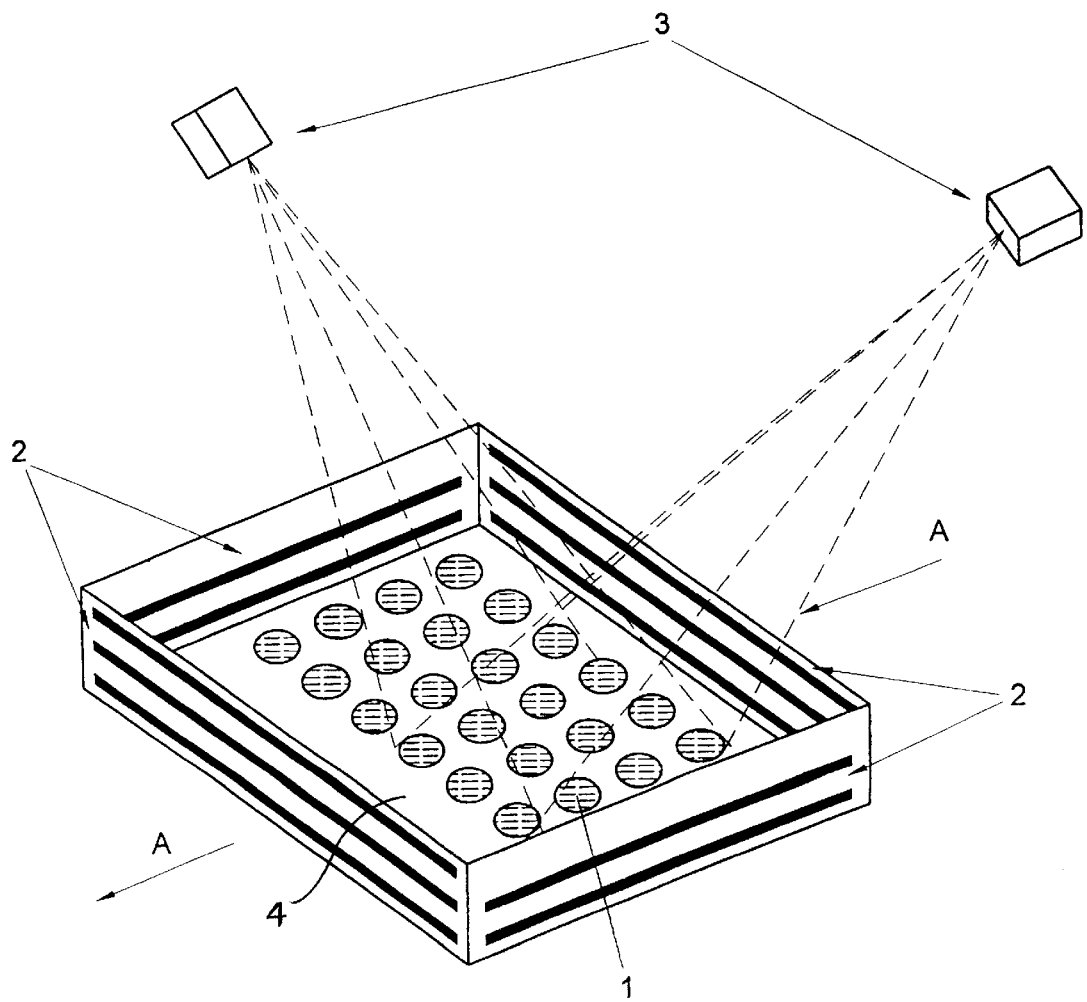
FIG. 1, showing schematically the device in accordance with the present invention, and FIG. 2, giving a scheme for processing signals as obtained when imaging the articles in accordance with the present invention.

In FIG. 1 articles, in particular eggs 1, are shown schematically while placed on a conveyor 4 (not shown in detail), the conveyor 4 moving in the direction as given by arrow A. Usually eggs placed on such a conveyor 4 are rolling about their main axis. During transport the eggs pass a source 2 of ultraviolet light. For example a source 2 may comprise a light box which supports several lamps or a combination of one or more lamps and one or more mirrors. The light reflecting from the eggs, mainly fluorescent light from the egg shells, is captured as an image by image receiving means of at least one camera 3.

For a skilled person it will be clear that many types of lamps or light sources irradiating ultraviolet light having emission spectra at least with wavelengths between 250 and 400 nm can be used. In special cases, for example for certain types of eggs, such as brown eggs, filters for blocking light having wavelengths which will disrupt or interfere with the inspection results, are employed advantageously. Suitable filters which filter wavelengths between 400 and 800 nm are applied. Preferably for brown eggs filters filtering wavelengths between 620 and 720 nm are employed. Furthermore in FIG. 1 exemplary positions are shown for two cameras arranged adjacent to a conveyor. Generally CCD type cameras which are sensitive for the fluorescent light can be employed. Filters as mentioned before can be arranged on the cameras.

It will be clear to those skilled in the art that the fluorescent light sensitiveness of the cameras has to be set in accordance with the situation of either unwashed or cleaned eggs. Of course there is the possibility for detecting and sorting blends of washed and cleaned eggs in one run.

Figure 2:
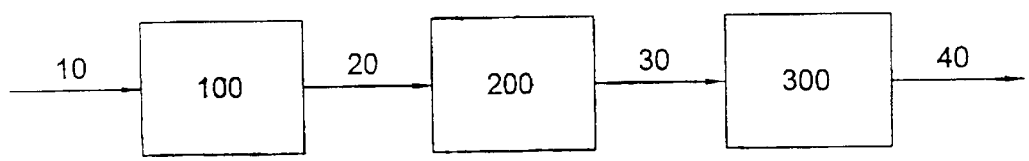

In FIG. 2 a scheme is shown for processing image signals as obtained by means of the above described cameras when imaging the articles. Fluorescent light 10 strikes one or more cameras 100. The image signals thus obtained represent image data 20 comprising information on values of black levels and positions of all the pixels. The data are processed in an image data processing unit 200 resulting in processed data 30. Subsequent to such processing, the data 30 are supplied to a unit 300 for comparing the data 30. Further to comparison the unit 300 is also capable for selecting the data, thus resulting in comparison data or selection data 40 respectively. The data 40 are used for control of for example an article sorting machine or a selection unit.

For those skilled in the art it will be clear that unit 200, generally being a computer, is capable for taking into account effects of shadowing in case of multi-side exposure, and consequently for carrying out standardizing the data 30 over the whole image field. Also corrections can be made for border effects i.e. effects of dirt present at the image border, thereby using well-known methods for projecting image data and comparing the projected data with well known egg characteristics. The values of black levels as mentioned before allow to determine contrast data for the pixels. After standardizing these contrasts for the whole image, details within the image can be made visible.

In order to obtain well usable images a background materials should have suitable color and light reflecting characteristics. Advantageously non-fluorescent materials are chosen.

The contrast data allow determination of both total egg surface areas and dirt surface areas.

For example methods for elimination of well-defined gray values are applied in order to arrive at suitable images.

By means of unit 300, preferably being a computer, for example a personal computer or a main frame computer, further determinations such as checking the contrast data with regard to limit or threshold values, are carried out. This means that by exceeding such limit or threshold values articles are considered no longer suitable for use or consumption and consequently have to be selected and sorted out.

All kinds of combinations of rotating the eggs and exposing the eggs to continuously, intermittently or pulsing irradiated light, or even combinations, can be employed. Corresponding data processing is used. In this respect, rotating and irradiating the eggs is self-evident. For pulsing irradiating all kinds of pulses can be applied, i.e. shorter or larger pulse durations, and high and low frequency pulses. Intermittent is defined as positioning the eggs in subsequent well-defined positions and imaging the eggs only in those positions.

Furthermore well known pattern recognition algorithms for dirt or cracks can be applied.

For a skilled person it may be clear that slight deviations from the method and device as explained above are also comprised by the present invention and by the appending claims.

What is claimed is:

1. A method for detecting dirt on eggs, comprising,
   exposing eggs to ultraviolet light,
   capturing images of the exposed eggs, said images comprising pixels, and
   determining within said images surface areas of dirt on the basis that egg shells are fluorescent whereas a dirt surface is not fluorescent by correlating data of contrast and data of position of said pixels.

2. Method according to claim 1, wherein for each egg the total surface area is imaged.

3. Method according to claim 1, wherein during said capturing images of the exposed eggs, said eggs are exposed from at least two sides.

4. Method according to claim 3, wherein the eggs are exposed continuously during rotation about an axis.

5. Method according to claim 3, wherein the eggs are exposed intermittently during rotation about an axis.

6. Method according to claim 5, wherein the eggs are exposed after every angle of rotation of 90°.

7. Method according to claim 1, wherein filters for filtering out light with wavelengths between 400 and 800 nm are arranged.

8. Method according to claim 7 wherein the filters are for filtering out light with wavelengths between 620 and 720 nm.

9. A method for selecting dirty eggs, comprising,
   supplying the eggs to be selected,
   exposing said eggs to ultraviolet light,
   capturing images of exposed eggs, said images comprising pixels,
   determining within said images surface areas of dirt on the basis that egg shells are fluorescent, whereas a dirt surface is not fluorescent by correlating data of contrast and data of position of said pixels,
   comparing said areas to reference areas having a limit value of an acceptable amount of dirt,
   determining eggs for which said limit has been exceeded,
   selecting said eggs for which said limit has been exceeded, and
   removing said eggs after said selecting.

10. Method according to claim 9, wherein for each egg the total surface area is imaged.

11. Method according to claim 9, wherein during said capturing images of the exposed eggs, said eggs are exposed from at least two sides.

12. Method according to claim 11, wherein the eggs are exposed continuously during rotation about an axis.

13. Method according to claim 11, wherein the eggs are exposed intermittently during rotation about an axis.

14. Method according to claim 13, wherein the eggs are exposed after every angle of rotation of 90°.

15. Method according to claim 9, wherein filters for filtering out light with wavelengths between 400 and 800 nm are arranged.

16. Method according to claim 15 wherein the filters are for filtering out light with wavelengths between 620 and 720 nm.

17. A device for detecting dirt on eggs, comprising,
support means for said eggs,
a source of ultraviolet light for exposing said eggs, characterized in that the device will comprise:
  a camera for imaging said eggs for obtaining images of said articles,
  an image processing means for determining data of contrast and data of position of pixels building up said images, and
  data processing means for correlating said data of contrast and said data of position on the basis that egg shells are fluorescent, whereas a dirt surface is not fluorescent in order thereby determine dirt surface areas of said supported eggs.

18. Device according to claim 17, wherein filters for filtering out light with wavelengths between 400 and 800 nm are arranged.

19. Device according to claim 18 wherein the filters are for filtering out light with wavelengths between 620 and 720 nm.

20. A device for selecting dirty eggs, comprising,
means comprising a conveyor for supplying and removing said eggs, for selecting and selected eggs respectively,
a source of ultraviolet light for exposing said eggs,
a camera for imaging said eggs for obtaining images of said eggs,
an image processing means for determining data of contrast and data of position of pixels building up said images, and
data processing means for correlating said data of contrast and said data of position on the basis that egg shells are fluorescent whereas a dirt surface is not fluorescent in order thereby determine dirt surface areas of said supported articles,
means for comparing said surface areas of dirt to reference areas having a limit value of an acceptable amount of dirt,
means for determining eggs for which said limit has been exceeded, and
means for selecting said eggs for which said limit has been exceeded.

21. Device according to claim 20, wherein said eggs are conveyed by means of a conveyor and rotate about an axis.

22. Device according to claim 20, wherein said eggs are exposed continuously.

23. Device according to claim 20, wherein said eggs are exposed intermittently.

24. Device according to claim 20, wherein said source is a light pulse generator.

25. Device according to claim 20, wherein filters for filtering out light with wavelengths between 400 and 800 nm are arranged.

26. Device according to claim 25, wherein the filters are for filtering out light with wavelengths between 620 and 720 nm.

* * * * *